United States Patent [19]

Weigert

[11] 4,061,685
[45] Dec. 6, 1977

[54] CATALYTIC SYNTHESIS OF PHENOLS

[75] Inventor: Frank Julian Weigert, Wilmington, Del.

[73] Assignee: E. I. Du Pont de Nemours and Company, Wilmington, Del.

[21] Appl. No.: 683,394

[22] Filed: May 5, 1976

Related U.S. Application Data

[63] Continuation-in-part of Ser. No. 547,959, Feb. 7, 1975, abandoned.

[51] Int. Cl.² ............................................. C07C 39/04
[52] U.S. Cl. ............................................... 260/621 G
[58] Field of Search ...................... 260/621 G, 621 R

[56] References Cited

U.S. PATENT DOCUMENTS

| 2,903,480 | 8/1959 | Toland | 260/621 G |
| 3,180,877 | 4/1965 | Benichou et al. | 260/621 G |

Primary Examiner—James O. Thomas, Jr.
Assistant Examiner—W. B. Lone
Attorney, Agent, or Firm—Anthony P. Mentis

[57] ABSTRACT

A phenol is produced by heating water and a cyclic or acyclic alkane or alkene of 6–10 carbon atoms at a temperature of 350° to 700° C in the presence of a metal oxide catalyst. Exemplary is the heating of water and cyclohexane in a nitrogen atmosphere and in the presence of $ZnO/TiO_2$ to produce phenol.

14 Claims, No Drawings

CATALYTIC SYNTHESIS OF PHENOLS

RELATED APPLICATIONS

This application is a continuation-in-part of copending application Ser. No. 547,959, filed Feb. 7, 1975, now abandoned.

BACKGROUND OF THE INVENTION

1. Field of the Invention

This invention concerns a process for producing phenols, and in particular to a new synthesis in which a nonaromatic hydrocarbon is reacted with water in the presence of a metal oxide catalyst.

2. Prior Art

Processes for producing phenol are known. L. F. and M. Fieser, "Advanced Organic Chemistry", Rheinhold Publishing Corp., New York, pages 745-747 (1961) describes several such processes including: (a) sulfonation of benzene, followed by alkali fusion; (b) nitration of benzene, reduction to aniline, formation of a diazonium salt, and finally hydrolysis; (c) formation of an aryl halide, followed by alkali hydrolysis; (d) formation of a hydroaromatic ketone, such as cyclohexanone by oxidation of cyclohexane, followed by dehydrogenation; and (e) oxidation of cumene to a hydroperoxide, followed by acid catalysis. Each of these processes suffers from one disadvantage or another.

U.S. Pat. No. 3,180,877 to Benichou et al. describes the catalyst oxidation of a hydrocarbon wherein a nonexplosive mixture of a hydrocarbon and air is heated to about 410° C in the presence of a catalyst to produce an oxygenated compound. The nonexplosive mixture is needed to avoid complete oxidation of the hydrocarbon to water, carbon monoxide and carbon dioxide, as would occur in the uncontrollable reaction engendered by an explosion, and such nonexplosive mixture is obtained by using a large excess of air. In the sole disclosed example, naphthalene and a very large excess of air (e.g., an eight-fold excess of oxygen compared to stoichiometric requirements) are passed through a series of catalyst beds composed of 8% vanadium oxide ($V_2O_5$) on an inert carrier to produce phthalic anhydride. The inlet and outlet temperature of each bed is 350° and 410° C, respectively. Cooling is provided by injection of water between successive stages to absorb the heat developed by the highly exothermic reaction, the "water being used because of its high heat of evaporation and of its substantial neutrality to the reaction in progress." The patent suggests that the process can be used to convert cyclohexane to phenol. Contrary to this suggestion, however, it has been found that the reaction of cyclohexane with large excess quantities of air in the presence of water and $V_2O_5$ catalyst on an inert carrier does not yield measurable quantities of phenol at temperatures of 350°, 400° or at 500° C.

DESCRIPTION OF THE INVENTION

In contrast to the above prior art, the present invention provides a process for the production of a phenol from a hydrocarbon wherein a cyclic or open-chain alkane or alkene of 6 to 10 carbon atoms having a continuous chain of at least six successive carbon atom each of which is bonded directly to no more than three other carbon atoms is reacted with water at a temperature of 350° to 700° C in the presence of a metal oxide catalyst selected from oxides of Al, Bi, Cd, Ce, Cr, Cu, Fe, In, Mn, Mo, Sn, Te, Th, Ti, U, V, W, Zn and Zr.

It is preferred to operate in a nonoxidative atmosphere (i.e., one in which molecular oxygen or similar oxidizing gases are absent). Generally, this leads to higher yields of phenolic compound per gram of catalyst with fewer undesired by-products. However, the synthesis can be carried out with as much as one mole, but preferably less than 0.4 mole, of molecular oxygen being present per mole of the hydrocarbon starting material, even though the maximum benefits of the process would not be obtained. The process can be carried out in an atmosphere which contains an inert gas such as nitrogen, helium, argon, neon and the like. A convenient method by which the oxygen may be excluded from the system is to simply pass steam and/or hydrocarbon continuously through a reactor containing the catalyst prior to heating the reactants and starting the phenol synthesis.

The hydrocarbons used as starting materials in the process are cyclic or acyclic (i.e., open chain) alkanes or alkenes having 6 to 10 carbon atoms. Each of these hydrocarbons has a continuous chain of at least six successive carbon atoms, none of which is bonded directly to more than three carbon atoms. The hydrocarbons are capable of aromatization. Specific hydrocarbons which are suitable for use in the process include cyclohexane, methylcyclohexane, n-butylcyclohexane, 1,2-dimethylcyclohexane, 1,4-dimethylcyclohexane, 1,4-diethylcyclohexane, cyclohexene, methylcyclohexene, ethylcyclohexene, propylcyclohexene, butylcyclohexene, dimethylcyclohexene, 1-methylcyclopentene, cyclohexadiene, methylcyclohexadiene, ethylcyclohexadiene, butylcyclohexadiene, dimethylcyclohexadiene, decalin, hexane, heptane, octane, nonane, decane, hexene, heptane, octene, nonene, decene, 2-methylhexane, 2-ethyloctane, 3-methylhexene, and the like. It is preferred that any hydrocarbon rings present should have six members, as for example cyclohexane or cyclohexene, which are preferred starting materials because they give high reaction rates and yields of product. Cyclohexane is the preferred starting material.

The amount of water relative to the hydrocarbon can vary over wide limits. It is preferred to use 5-95% by weight of water based on the total weight of water and the hydrocarbon but more preferred is a range of 15-60% by weight of water.

Generally, the phenol synthesis of the invention can be carried out at a temperature range of 350° to 700° C. Above 700° C, undesirable by-products usually form. Below 350° C, phenol is not formed. Thus, it is generally preferred to operate in a temperature range of 450° to 650° C, with a range of 475° to 550° C being most preferred.

The term "metal oxide" includes binary oxides, ternary oxides, quaternary oxides and higher polynary oxides, as well as solid solutions and nonstoichiometric oxides. The term includes a single oxide; mixed oxides of a single metal in different valence states such as FeO and $Fe_2O_3$, etc.; and mixed oxides of different metals such as physical mixtures of zinc oxide and aluminum oxide, etc. Also included are mixed oxides which can be described as compounds, including cerium zirconate, cadmium stanate, zinc stannate, ferrous titanate, zinc metavanadate, zinc pyrovanadate, zinc orthovanadate, cadmium molybdate, cerium molybdate, manganese molybdate, zinc molybdate and zinc titanate, etc. The invention is a broad one in that all combinations of the metal oxides, in any proportion, are operative.

Combinations of two or more of the metal oxide catalysts are especially useful in providing desired activity, selectivity, long life, and the like and are preferred for use in this process. Generally two to five metal oxides are employed in a catalyst since such compositions are more economic to prepare than those containing more than five components. Relatively inert catalyst carriers or diluents may be present, e.g. carbon, silicon carbide, silica, magnesia, boron phosphate, and the like, as known in the art. Other elements such as Ag, Ba, Ca, Hg, K, La, Mg or Ni may be present in the oxide catalyst for their beneficial effects. Such beneficial effects include increasing catalyst life, reduction of by-products, and the like.

Specific combinations of catalysts which are particularly preferred for their ability to convert cyclohexane and water to phenol include oxides of (a) zinc and vanadium, (b) zinc and titanium, and (c) zinc, titanium and lanthanum.

The catalysts may be made by any conventional or suitable method known in the art, such as direct heating of the elements in air. Other methods of obtaining metal oxides include impregnation, evaporation, or precipitation, each followed by calcination. The catalysts should be as pure as possible and when, for example, a metal salt, such as a halide is used as a starting material to prepare the metal oxide catalyst, it is beneficial to wash the prepared catalysts thoroughly with water to free it as much as possible of any remaining anion, e.g., halide, sulfate, etc.

The catalysts may be reactivated by burning off any carbonaceous deposit which may form after use. The burning may be done, for example, by flushing the reactor with heated air or oxygen for a suitable time, as is known in the art.

The reaction can be carried out at any pressure but pressures in the range 0.5 to 20 atmospheres are preferred.

The contact time of the reactants with the catalyst may range from about 0.01 second to about 10 minutes. A preferred range is about 0.1 second to about 2 seconds.

The catalyst can be present in any amount since it merely needs to be present to contact the reactants in order to exert its catalytic effect, as is known in the art.

After passage as gases through the catalyst bed, or a series of beds, the process streams may be cooled to form aqueous and organic liquid phases. The phenolic products are distributed between the two phases, with phenol itself usually found predominantly in the aqueous phase. The products may be separated by known methods, such as extraction with an appropriate solvent or absorption on charcoal followed by distillation. Any portion of the hydrocarbon that is not reacted may be recycled.

SPECIFIC EMBODIMENTS OF THE INVENTION

In the following illustrative examples all parts are by weight and all temperatures are Centigrade unless otherwise stated.

In the examples the catalyst was charged into a tubular reactor and the reactor heated at the specified temperature. Hydrocarbon and water were introduced and reacted in a nonoxidative atmosphere and the rate of introduction measured as liquid volume per hour. Generally a pre-heated inert gas such as nitrogen was used as a carrier and diluent for the reactants. The contact time was usually greater than 0.1 second and not over 2 seconds.

The reaction products were analyzed by gas chromatography using Tenax ® (porous 2,6-diphenyl-p-phenylene oxide) in 60 to 80 mesh size in an 8 feet × 1/8 inch [2.4 meters × 3.2 mm] stainless steel column at 190° while passing helium gas through at 75 ml per minute. The reaction times were 0.3 minutes for water; 4.4 minutes for 1,4-butanediol (internal standard); and 5.5 minutes for phenol. A color test using a mercury reagent was used to determine the presence of phenols as follows: A drop of the aqueous solution was mixed with a drop of a reagent solution and left for a few minutes. If no change occurred, the mixture was heated briefly to boiling. A red color formed in the presence of phenols. The reagent solution was prepared by dissolving one part mercury in one part fuming nitric acid and diluted with 2 parts water. With the mercury reagent color test, $10^{-5}$ mole of phenol per liter of water is barely detectable while $10^{-3}$ mole per liter is readily detectable. NMR spectroscopy was employed in some instances, particularly when alkyl cyclohexanes were used. Ultraviolet spectroscopy was used to assay for the total phenolic content in the aqueous phase by measuring the absorbance at 2700 A. The phenolic products were distributed between aqueous and organic phases, but phenol itself was predominantly in the aqueous phase.

Example I

In this example, a series of runs are described in which cyclohexane and water were reacted in the presence of one or more metal oxide catalysts to produce phenol. The reaction, which was conducted in the gas phase, is believed to be represented by the following:

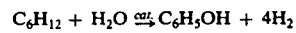

$$C_6H_{12} + H_2O \rightleftharpoons C_6H_5OH + 4H_2$$

Each run was carried out in a tubular reactor measuring 7 inches [17.8 cm] long by ½ inch [1.27 cm] in diameter made of borosilicate glass (i.e., Corning Glass Vycor ® which is 96% $B_2O_3$ and 3% $SiO_2$). About 3 $cm^3$ of catalyst was placed within the reactor and the assembly was then heated and maintained at constant temperature. A nonoxidative atmosphere was established by a flow of 20 $cm^3$ per minute of preheated nitrogen. Cyclohexane and water were introduced into the nitrogen stream, each at a rate of 6 ml of liquid per hour. The nitrogen heated and immediately vaporized the cyclohexane and water and acted as an inert carrier and diluent for the reactants. The reactants contacted the catalyst for about one second. Atmospheric pressure was maintained. Product was collected in a cold trap operating at 0° C.

The results of these runs and the temperatures at which they were carried out are summarized in Table I. A "space-time yield" is recorded for each catalyst tested. Space-time yield is defined as the milligrams of phenol produced per hour for each gram of catalyst present.

Part A of Table I summarizes runs a-1 through a-18 in each of which only one metal oxide catalyst was used. Part B of Table I summarizes the runs in which the catalyst contained oxides of more than one metal. In runs b-1 through b-4 the catalysts includes oxides of zinc and titanium, a combination of oxides preferred for use in the present process. In runs c-1 and c-2, another preferred catalyst combination, containing oxides of zinc and vanandium, was used. Catalysts of runs d-1 through d-3 included oxides of zinc and metals other than titanium or vanadium. In runs e-1 through e-8, the catalysts included oxides of vanadium and metals other than zinc. In runs f-1 through f-8 the catalysts contained still other combinations of metal oxides. As can be seen in Table I, the combined oxides generally provided higher space-time yields than the one-metal oxides.

TABLE I
PHENOL FROM CYCLOHEXANE AND WATER

A. Catalysts Containing One Metal Oxide

| Run No. | Catalyst | Space-Time Yield | | | |
|---|---|---|---|---|---|
| | | 450° C | 500° C | 525° C | 550° C |
| a-1 | $Al_2O_3$ | — | — | 0.06 | — |
| a-2 | $Bi_2O_3$ | 0.3 | — | — | 0.17 |
| a-3 | CdO | 0.18 | — | — | 0.26 |
| a-4 | $CeO_2$ | 0.12 | — | — | 1.7 |
| a-5 | $Cr_2O_3$ | 0.29 | — | — | 2.1 |
| a-6 | CuO | 0.05 | — | — | 0.02 |
| a-7 | $Fe_2O_3$ | — | — | — | 8.3 |
| a-8 | $In_2O_3$ | 0.36 | — | — | 4.4 |
| a-9 | MnO | 0.28 | — | — | 0.21 |
| a-10 | $MoO_3$ | * | — | — | * |
| a-11 | SnO | 0.10 | — | — | 0.08 |
| a-12 | $TeO_2$ | * | * | — | * |
| a-13 | $ThO_2$ | 0.72 | — | — | 0.52 |
| a-14 | $TiO_2$ | 0.24 | — | — | 4.9 |
| a-15 | $V_2O_5$ | — | 4.4 | 4.3 | — |
| a-16 | $WO_3$ | 0.07 | — | — | 0.12 |
| a-17 | ZnO | — | 0.2 | 0.2 | — |
| a-18 | $ZrO_2$ | 0.14 | — | — | 0.09 |
| +a-19 | Uranium oxide | — | * | — | — |

*Space-time yield not measured quantitatively but the presence of phenol was verified by the mercury reagent color test.
+Uranium oxide (from calcined uranyl nitrate) with flow rate of cyclohexane of 2 ml/hr, and water of 4.5 ml/hr and nitrogen at 20 ml/minute at 500° for 20 minutes.

B. Catalysts Containing Oxides of More Than One Metal

| Run No. | Catalysts | Space-Time Yield | |
|---|---|---|---|
| | | 450° C | 550° C |
| b-1 | *4Ti/Zn/La oxides | 1.8 | 36 |
| b-2 | 4Ti/Zn/Ce oxides | 2.0 | 16 |
| b-3 | 4Ti/Zn/Mg oxides | 1.4 | 34 |
| b-4 | Ti/Zn/Bi/Mo/Al oxides | 0.86 | 2.6 |
| c-1 | $ZnO/V_2O_5/Al_2O_3$ | 16 | 27 |
| c-2 | $ZnCeV_2O_8$ | 14 | 34 |
| d-1 | 4Zn/Cr oxides | 0.78 | 5.6 |
| d-2 | CdO/ZnO | 3.0 | 84 |
| d-3 | $Fe_2O_3$/ZnO | 1.9 | 46 |
| e-1 | 2Ag/4V oxides | 1.5 | 3.3 |
| e-2 | 5Cr/V oxides | 0.36 | 10.7 |
| e-3 | Cu/2V oxides | 2.3 | 5.2 |
| e-4 | $FeVO_4$ | 16.3 | 27 |
| e-5 | $In_2O_3/V_2O_5$ | 3.0 | 17.6 |
| e-6 | $NiSnV_2O_8$ | 12.2 | 24 |
| e-7 | Sn/2V oxides | 3.3 | 19 |
| e-8 | $Zr_2V_2O_7$ | 0.18 | 1.5 |
| f-1 | $Bi_2O_3/2MoO_3$ | 0.68 | 1.2 |
| f-2 | $Ca_{0.9}Cd_{0.1}TiO_3$ | 0.21 | 12.9 |
| f-3 | $Cr_2O_3/In_2O_3$ | 0.46 | 8.2 |
| f-4 | $CuO/Al_2O_3$ | 0.37 | 1 |
| f-5 | $Fe_2(MoO_4)_3$ | 10.3 | 0.54 |
| f-6 | $MnMoO_4$ | 0.16 | 0.66 |
| f-7 | $In_2O_3/TiO_2$ | 6.1 | 49 |
| f-8 | 2Zr/Cr oxides | 0.78 | 9.8 |

*In this example the catalyst components are molar ratios.

EXAMPLE II

The apparatus and general procedures of Example I were used in this example to produce phenols from water and alkanes other than cyclohexane.

At flows of 5.6 ml/hr each of water and 1,4-dimethylcyclohexane, with a $ZnO/V_2O_5$ catalyst present, and temperature maintained at 550° C, phenolic compounds, including phenol and cresols, were obtained as shown by color tests, gas chromatography and mass spectroscopy. Similarly, when methylcyclohexane was used, phenol and cresols were also produced.

By the same procedure as above, but with a catalyst containing 90% $TiO_2$ and 10% ZnO, with temperatures of 450°, 500°, and 550° C, and with ethylcyclohexane or t-butylcyclohexane as the starting hydrocarbon, phenolic products were again obtained. During the reaction, some of the alkyl groups of the alkylcyclohexanes were removed.

Phenol was produced by the same general procedure as above from hexane or heptane or octane. In these runs, 4.0 grams of a catalyst consisting of 12% $Cr_2O_3$, 2% MgO, and 86% $Al_2O_3$ were present, the alkane flow was 7.5 ml/hr and the temperature was maintained at 540°, 575° and 600° C. The phenol product was detected by mercury reagent color testing of the aqueous layer of the effluent stream.

EXAMPLE III

In this Example, the process of the invention is illustrated with alkene starting hydrocarbons.

The same catalyst and flow rates as in the last paragraph of Example II were used to produce a phenol, with hexene being substituted for the alkanes. Use of heptene in place of hexene and a temperature of 575° C resulted in a space-time yield of 2 mg of phenol per hour per gram of catalyst and an aqueous effluent layer that contained 0.1% phenol. Substitution of 2-octene and use of a temperature of 660° C resulted in a space-time yield of phenols of 6 mg/hr/g of catalyst.

A tubular reactor was charged with 2 g of 10% ZnO on $TiO_2$, heated at 525° and cyclohexene and water introduced at feed rates of 30 ml/hr each, with nitrogen at 20 ml/min. Phenol was formed at 350 mg/hr/g of catalyst. At a feed rate of 3 mg/hr each of cyclohexene and water, 70 mg of phenol was formed/g of catalyst/hr.

With the reactor being fed with 5.6 ml/hr of cyclohexene, 3.6 ml/hr of water and 20 ml/min of nitrogen carrier gas, introduced at 525° C and a 0.5 gram of catalyst being present in the form of oxides of zinc and vanadium (with a 1:2 molar ratio of Zn to V), 23.8 mg of phenol were obtained in 14.4 minutes, which corresponds to a space-time yeild of 198 mg/hr/g. After an additional 14.3 minutes of operation, another 28.7 mg of phenol were obtained, which corresponds to 240 mg/hr/g. However, after another 18.5 minutes, the rate of phenol production was found to have decreased, with only 15.4 mg of phenol having been produced and the space-time yield correspondingly decreased to 100 mg/hr/g. Use of this same procedure, with 1,3-cyclohexadiene substituted for the cyclohexene, produced an average of 24 mg of phenol per hour per gram of catalyst over five 10-minute periods.

EXAMPLE IV

This example summarizes the space-time yields of phenol obtained by the reaction of cyclohexane and water in the presence of various zinc oxide/vanadia catalysts with a contact time of about 1 second. The general method and apparatus of Example 1 were used with 1.5 grams of catalyst, 20 cm³/min of preheated nitrogen as carrier and the flow rates and temperatures given below.

A. A $ZnO/V_2O_5$ catalyst (i.e. molar ratio of zinc to vanadium = 1:2) was prepared by mixing zinc nitrate with ammonium vanadate in water, followed by evaporation and heating to about 435° C. The following table presents the results of runs at different temperatures under two sets of flow conditions.

TABLE II

| Flow, ml/hr | | Temperature | Space-Time Yield |
|---|---|---|---|
| Cyclohexane | Water | ° C | mg/hr/g |
| 5 | 2 | 450 | 0.8 |
| | | 475 | 1.6 |
| | | 500 | 3.8 |
| | | 525 | 6.8 |
| | | 550 | 9.5 |
| 1.2 | 0.6 | 600 | 10.3 |
| | | 625 | 9.5 |
| | | 650 | 4.4 |
| | | 675 | 1.6 |

The space-time yields for temperatures of 450°–525° C are the averages of two runs; at 550° C, the average of three runs; and at 600° to 675° C, the results of single runs.

B. A series of ten zinc oxide/vanadia catalysts were prepared by mixing zinc nitrate with ammonium vanadate in water, evaporating the water, and then heating to about 425° C. Each of the catalysts was tested as in part (A) but with the flows being 5.6 ml (liquid) per hour of cyclohexane and 3.6 ml/hr of water and with the reaction conducted at 525° C. As shown in the following table, summarizing the space-time yields obtained (mg phenol/hr/g of catalyst), a maximum yield was obtained with catalysts having molar ratios of zinc to vanadium 1:2 to 1:3, with the highest yield at a ratio of 1:2.5.

TABLE III

| Molar Ratio Zinc/Vanadium | Space-Time Yield |
|---|---|
| 1:0.3 | 11 |
| 1:1 | 11 |
| 1:1.5 | 17 |
| 1:2 | 63 |
| 1:2.4 | 83 |
| 1:2.5 | 100 |
| 1:2.6 | 88 |
| 1:2.8 | 76 |
| 1:4 | 34 |

C. Similar results were obtained with catalysts of oxides of zinc and vanadium prepared by an impregnation technique in which zinc oxide was slurried in aqueous solution containing ammonium vanadate, evaporated to dryness and then calcined for about 16 hours at 450° C. The following Table IV lists the percent $V_2O_5$ on ZnO and the space-time yield for phenol formation.

TABLE IV

| % $V_2O_5$ | Space-Time Yield |
|---|---|
| 16 | 65 |
| 4 | 28 |
| 2 | 30 |

EXAMPLE V

The apparatus and general procedure of Example I were used to determine the space-time yields for phenol formation over a range of cyclohexane and water feed rates. The operation was carried out at 525° C, with 2.0 grams of catalyst and a flow of 20 cm³ per minute of nitrogen carrier gas. The catalyst was 10% ZnO, with the remainder $TiO_2$. The results are summarized below.

TABLE V

| Feed Rate, ml per hour | | Space-Time Yield |
|---|---|---|
| Cyclohexane | Water | mg/hr/g |
| 1 | 10 | 9.5 |
| 1 | 1 | 13 |
| 3 | 3 | 29 |
| 5 | 5 | 50 |
| 10 | 10 | 39 |
| 10 | 1 | 21 |

EXAMPLE VI

The regeneration of catalysts is illustrated in this example with oxides of zinc and titanium. A tubular reactor similar to that of Example I was used.

A. Cyclohexane and water were passed through the reactor, each at a rate of 6 ml/hr along with 20 cm³/min of nitrogen for a period of 4½ hours. The reactor contained 2.8 grams of a $Zn_{0.8}Fe_{0.133}Ti_5O$ catalyst and was heated to 525° C. For the first 25-minute period of operation the space-time yield was 66 mg/hr of phenol per gram of catalyst. However, by the end of the 4½ hours, the space-time yield had decreased to 9 and the catalyst had acquired a black color. At this point, the feeding of cyclohexane and water was stopped while heating of the reactor was continued and air was passed through the hot catalyst for four minutes. The original tan color of the catalyst was restored. Subsequently a 35-minute run with the original conditions restored indicated that the regenerated catalyst operated with a 64 mg/hr/g space-time yield.

B. A similar test was run with 2 grams of catalyst consisting of 5.4% ZnO on $TiO_2/Al_2O_3$ at 525° C and flows of 3 ml/hr each of cyclohexane and water to give the following space-time yields:

| Minutes of Running | Space-Time Yield mg/hr/g |
|---|---|
| 45 | 19 |
| 184 | 26 |
| 301 | 7.5 |

At this point, the feed of cyclohexane and water was stopped and air passed through the reactor for 30 seconds while temperature was maintained at 525° C. After restoration of the original conditions, the following results were obtained:

| Minutes of Running | Space-Time Yield mg/hr/g |
|---|---|
| 52 | 20 |
| 144 | 15 |

EXAMPLE VII

A tubular reactor measuring 14 inches [35.6 cm] long and ⅞ inch [22.2 mm] in inner diameter was charged with 14 grams of a catalyst containing oxides of zinc, titanium and cerium. The catalyst was prepared as follows: A 4000-ml aqueous solution containing 285 grams of $TiCl_4$, 11.5 grams of $Zn(NO_3)_2 \cdot 6H_2O$ and 0.21 gram of $Ce(NO_3)_3 \cdot 6H_2O$ was mixed with 281.4 grams of urea; refluxed for about 17 hours; and then filtered. The filtered solids were then washed by being thoroughly mixed with 1500 ml of distilled water and being refiltered. The washing procedure was then repeated twice. The final filtered solids were dried for 24 hours at 100°

C in a vacuum oven and then calcined in flowing air for 3 hours at 525° C.

A preheat section, filled with silicon carbide chips, was located within the tubular reactor just upstream of the catalyst. The reactor and its contents were heated to 525° C by hot air flowing through the system. The flow of air was stopped and replaced by flows of 27 ml/hr of cyclohexane and 9 ml/hr of water, fed at atmospheric pressure for 1½ hours while temperature was maintained at 525° C. At this point, the pressure in the system was raised to 2.7 atmospheres and all other conditions held constant. The phenol content of the aqueous product layer was analyzed by gas chromatography. The results, starting from the time that cyclohexane and water were fed to the system, were as folows:

| Time Period (hours) | Pressure (atmospheres) | % Phenol in Aqueous Layer |
|---|---|---|
| 0–0.5 | 1.0 | 3.6 |
| 0.5–1.0 | 1.0 | 2.4 |
| 1.0–1.5 | 1.0 | 0.85 |
| 1.5–2.0 | 2.7 | 0.75 |
| 2.0–2.5 | 2.7 | 0.33 |
| 2.5–3.0 | 2.7 | 0.13 |

After regeneration of the catalyst by passing air over it while hot, the higher pressure operating conditions were reestablished and within the first succeeding half-hour period, the phenol content was measured to be 3.8 weight percent.

EXAMPLE VIII

In this example the process of the invention was carried out in the presence of an inert gas or in the presence of minor amounts of molecular oxygen.

A tubular quartz reactor, measuring 50 cm long and 2.5 cm in diameter was loaded with 7.56 grams of a catalyst consisting of 15% zinc oxide on $TiO_2$. The system was heated to 525° C and 66 cm³/minute of helium, 10 ml/hr of water and 10 ml/hr of cyclohexane were fed through the system for 30 minutes. A cooled trap was used to collect the liquid product. Similarly, after the catalyst was regenerated by heating in air for 30 minutes at 500° C, the test was repeated with air being substituted for the helium. The amount of air used was about 1.9 moles per mole of cyclohexane.

These two tests were then repeated with 9.42 grams of a catalyst consisting of 10% $V_2O_5$ on $Al_2O_3$ in place of the $ZnO/TiO_2$ catalyst. The aqueous layer produced in each test was analyzed for phenol by ultraviolet spectroscopy and the organic layer was analyzed by gas chromatography. The results were as follows:

TABLE VI

| Catalyst | 15% $ZnO/TiO_2$ | | 10% $V_2O_5/Al_2O_3$ | |
|---|---|---|---|---|
| Gas Present | He | Air | He | Air |
| U.V. Analysis for phenol Space-time yield | 47.3 | 32.0 | 0.23 | 0.39 |
| G.C. Analysis Mole % | | | | |
| Methylcyclopentane | 0.24 | 0.25 | 0.27 | 0.30 |
| Cyclohexane | 92.62 | 87.83 | 90.16 | 77.68 |
| Cyclohexene | 0.45 | 0.39 | 2.65 | 3.42 |
| Benzene | 6.65 | 11.4 | 6.88 | 18.53 |
| Toluene | 0.03 | — | 0.02 | 0.04 |

These results show the superiority in yield of the preferred $ZnO/TiO_2$ combination of metal oxides over the $V_2O_5/Al_2O_3$ combination as catalyst. They also show that the presence of molecular oxygen, with the preferred combination, results in lower yield of phenol and in more production of potentially undesirable by-product benzene. Athough the results with the $V_2O_5/Al_2O_3$ catalyst do not show the same reduction in space-time yield when molecular oxygen is present, they do show a large increase in the benzene production.

COMPARATIVE EXAMPLE

The apparatus of Example I was charged with two grams of a catalyst consisting of 10% $V_2O_5$ on $Al_2O_3$ (Harshaw 0501). Flows of 0.31 ml/hr of cyclohexane, 1.1 ml/hr of water and 130 cm³/min of air were established. The amount of air used was in the ratio of about 120 moles of air to 1 mole of cyclohexane. The effluent liquid stream was analyzed for phenol by the mercury reagent color test after the system was operated (a) for 15 minutes at 350° C, (b) for 22 minutes at 400° C and (c) for 29 minutes at 500° C. No phenol could be detected in the effluent from these tests.

Upon completion of the above-described three runs, the flow of air was stopped and replaced by a flow 10 cm³/min of nitrogen carrier gas and the system operated at 500° C for 22 minutes. In constrast to the results obtained when a large amount of oxygen was present in the system, analysis for phenol by the mercury reagent color test in the run using nitrogen clearly established the presence of phenol in the effluent product.

I claim:

1. A process which consists essentially in reacting a cyclic or an open-chain alkane or alkene of 6 to 10 carbon atoms having a continuous chain of at least six successive carbon atoms, each of which is bonded directly to no more than three carbon atoms, with water in a nonoxidative atmosphere at a temperature of 350° to 700° C and at a contact time of about 0.01 second to about 10 minutes, in the presence of a metal oxide catalyst selected from oxides of Al, Bi, Cd, Ce, Cr, Cu, Fe, In, Mn, Mo, Sn, Te, Th, Ti, U, V, W, Zn and Zr to produce a phenol.

2. A process of claim 1 in which the hydrocarbon reactant is cyclohexane.

3. A process of claim 1 in which the hydrocarbon reactant is cyclohexene.

4. A process of claim 1 in which the amount of water used is 5–95% by weight based on the total weight of hydrocarbon and water.

5. A process of claim 1 in which the amount of water used is 15–60% by weight based on the total weight of hydrocarbon and water.

6. A process of claim 1 where the temperature is 450°–650° C.

7. A process of claim 1 where the temperature is 475–550° C.

8. A process of claim 1 where the contact time is 0.1–10 seconds.

9. A process of claim 1 in which the catalyst contains two or more of the oxides.

10. A process of claim 1 in which the catalyst contains two to five of the oxides.

11. A process of claim 1 in which cyclohexane is reacted to form phenol and the catalyst contains oxides of (a) zinc and vanadium, (b) zinc and titanium or (c) zinc, titanium and lanthanum.

12. A process of claim 1 in which the catalyst contains zinc oxide and vanadium oxide.

13. A process of claim 1 in which the catalyst contains zinc oxide and titanium oxide.

14. A process of claim 1 in which the catalyst contains zinc oxide, titanium oxide and lanthanum oxide.

* * * * *